United States Patent [19]

Brooks

[11] 4,076,832
[45] Feb. 28, 1978

[54] CYCLODIENE INSECTICIDES

[75] Inventor: Gerald Thomas Brooks, Burgess Hill, England

[73] Assignee: National Research Development Corporation, England

[21] Appl. No.: 739,323

[22] Filed: Nov. 5, 1976

[30] Foreign Application Priority Data

Nov. 6, 1975 United Kingdom ............... 46077/75

[51] Int. Cl.$^2$ .......................................... C07D 303/08
[52] U.S. Cl. ............................... 424/278; 260/348 C; 204/158 R
[58] Field of Search ..................... 260/348 C; 424/278

[56] References Cited

PUBLICATIONS

Journal Gen. Chemistry of the USSR, vol. 29 (1959), pp. 2797–2799.

Primary Examiner—Norma S. Milestone
Attorney, Agent, or Firm—Jacobs & Jacobs

[57] ABSTRACT

Analogues of dieldrin containing a reduced number of chlorine atoms are described, notably 2,10-syn-bisdechlorodieldrin and 2,3,10-syn-trisdechlorodieldrin. These have varying toxicities towards various insect species but offer the advantage of improved biodegradability.

6 Claims, No Drawings

CYCLODIENE INSECTICIDES

This invention relates to insecticides and more particularly to cyclodiene insecticides.

Among the class of cyclodiene insecticides Dieldrin has achieved prominence and has been used for many years. However the high chlorine content and hence poor biodegradability of this compound are factors which make its use increasingly questionable.

It has now been found that certain compounds related to Dieldrin have comparable levels of toxicity towards insects but are especially attractive on account of their reduced chlorine content.

The present invention comprises 2,10-syn-bisdechlorodieldrin and 2,3,10-syn-trisdechlorodieldrin, being compounds of structural formula

[structural formula]

wherein X is H or Cl.

These compounds are toxic to tsetse fly, stable fly, housefly, and blowfly and are biodegradable.

The compounds of the present invention can be prepared from dieldrin by successive replacement of vinylic chlorine atoms in dieldrin by hydrogen followed by replacement of chlorine at the 10-carbon atom. The latter step results in a mixture of syn- and anti-dechloro isomers which can be separated by fractional crystallisation and chromatographically. The anti-dechloro isomer is relatively inactive. Alternatively the chlorine atoms may be replaced in the reverse order.

Replacement of vinylic chlorine can be achieved by photodechlorination under the influence of ultra-violet light. Replacement of chlorine at the dichloromethano bridge can be achieved by reduction with certain metal hydrides e.g. tri-n-butyl tin hydride in presence of a free radical initiator or with a mixture of sodium borohydride and a cobaltous salt.

In a further alternative method, the starting material can be bis-2,3-dechlorodieldrin which can be converted into the desired 10-syn-dechloroderivative in one stage.

The invention is illustrated in the following Examples:

EXAMPLE 1

To produce 2,10-syn-bisdeclorodieldrin, Dieldrin (0.25 millimols) is treated under reflux in benzene (0.5 ml) with tri-n-butyl tin hydride (80 microliters) in presence of $\alpha$-$\alpha^1$ azobis-isobutyronitrile (0.5 mg) for 1 – 2 hours. Conversion of the reactant is monitored by thin layer chromatography on aluminium plates, with hexane/ether (3:1). The reaction mixture is precipitated with an equal volume light petroleum ether (40° – 60°) and the 10-syn-dechlorodieldrin separated by recrystallisation from methanol or by TLC or column chromatography on alkaline alumina using ether/light petroleum ether as eluant.

The product is dissolved in hexane and irradiated for five hours in a silica spectrophotometer cell (1 or 2 cm path) using a Camag Universal UV lamp type TL-900 (254 nm).

The desired product has m.p. 148° – 150° C.

To produce 2,3,10-syn-trisdechlorodieldrin, Example 1 is repeated except that the irradiation step is conducted with a more powerful source of radiation, a Hanovia U.V. 5,500 medium pressure arc.

The product has m.p. 163° – 165° C. Its toxicity to blowflies compares well with that of dieldrin i.e. $LD_{50}$ 0.02 micrograms (dieldrin 0.017).

The 2,3-dechloro compound of the present invention can be converted into the corresponding 2,3-epoxide by treatment with peroxytrifluoroacetic acid.

The compounds may be used in combination with synergists, e.g. sesamex or piperonylbutoxide.

What is claimed is:

1. A compound selected from the group consisting of a syn-dechloro dieldrin derivative of the formula:

[structural formulas]

and

[structural formula]

2. 2,10-syn-bisdechlorodieldrin.
3. 2,3,10-syn-trisdechlorodieldrin.
4. The 2,3-epoxide of the compound of claim 3.
5. An insecticidal composition comprising a compound according to claim 1.
6. An insecticidal composition according to claim 5 containing an insecticidal synergist.

* * * * *